United States Patent [19]
Albertsen et al.

[11] Patent Number: 5,432,068
[45] Date of Patent: Jul. 11, 1995

[54] CONTROL OF MALE FERTILITY USING EXTERNALLY INDUCIBLE PROMOTER SEQUENCES

[75] Inventors: Marc C. Albertsen, Ankeny; Larry R. Beach, Des Moines; John Howard, West Des Moines; Gary A. Huffman, Des Moines, all of Iowa; Loverine Taylor, Pullman, Wash.

[73] Assignee: Pioneer Hi-Bred International, Inc., Des Moines, Iowa

[21] Appl. No.: 848,433

[22] Filed: Mar. 9, 1992

Related U.S. Application Data

[63] Continuation-in-part of Ser. No. 537,183, Jun. 12, 1990.

[51] Int. Cl.$^6$ .......................... C12N 15/00; A01H 1/00
[52] U.S. Cl. ............................... 435/172.3; 435/172.1; 47/58; 536/24.1; 536/24.5
[58] Field of Search ............... 435/172.2, 172.1, 172.3; 47/58.03, 58.05; 536/24.1, 24.5, 23.1

[56] References Cited

FOREIGN PATENT DOCUMENTS

| | | | |
|---|---|---|---|
| 4945690 | 1/1990 | Australia | C12N 15/82 |
| 329308 | 3/1989 | European Pat. Off. | C12N 15/00 |
| 8910396 | 4/1989 | WIPO | C12N 5/00 |
| 9109957 | 7/1991 | WIPO | C12N 15/82 |

OTHER PUBLICATIONS

Coe et al. (1981) "The Journal of Heredity" vol. 72 pp. 318-320.
Ryder et al. (1989) PNAS vol. 81, pp. 5724-5728.
Koller et al. (1989) PNAS vol. 86, pp. 8932-8935.
Balcells, L., et al., "Transposons as Tools for the Isolation of Plant Genes", *Tibtech*, vol. 9, Jan., 1991.
Chandlee, J., "The Utility of Transposable Elements as Tools for the Isolation of Plant Genes", *Physiologia Plantarum*, 79:105-115, Copenhagen, 1990.
Chandler, V., et al., "The *Mu* Elements of *Zea mays*", *Advances in Genetics*.
Hanson, D., et al., "Characterization of a Pollen-Specific cDNA Clone from *Zea mays* and Its Expression", *The Plant Cell*, vol. 1, 173-179, Feb., 1989.
Herdenberger, F., et al., "Isolation of Flower-Specific cDNA Clones from Sunflower", *Plant Science*, 69:111-122, 1990.
Izawa, T., et al., "Introduction and Transposition of Maize Transposable Element Ac in Rice", *Mol. Gen. Genet.*, vol. 227, No. 3, pp. 391-396, 1991.
Mascarenhas, J., "The Isolation and Expression of Pollen-Expressed Genes", *Current Science*, vol. 58, No. 18, pp. 1008-1015, Sep. 20, 1989.
Pear, J., et al., "Isolation and Characterization of a Fruit-Specific cDNA and the Corresponding Genomic Clone from Tomato", *Plant Molecular Biology*, 13:639-651, 1989.

(List continued on next page.)

*Primary Examiner*—Gary Benzion
*Attorney, Agent, or Firm*—Patricia A. Sweeney

[57] ABSTRACT

An inducible promoter is used to regulate expression of a gene which is known to be critical to male fertility. The selected gene's control sequences are modified so that it is normally "off" and as a result the plants are male sterile. When it is desired to reproduce the male sterile plants, male fertility is restored by treating the plants with a non-phytotoxic chemical which induces expression of the critical gene. A critical gene is one which affects flavonol production and in particular compounds of the formula:

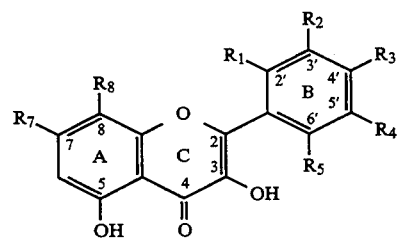

wherein $R_1$, $R_2$, $R_3$, $R_4$, $R_5$, $R_7$, and $R_8$, are hydrogen, hydroxyl or alkoxy having from 1 to 4 carbon atoms. Particularly preferred flavonols include galangin, kaempferol, iso-rhamnetin, quercetin and morin.

15 Claims, 5 Drawing Sheets

OTHER PUBLICATIONS

Peterhans, A., et al., "Intrachromosomal Recombination in Plants", *The EMBO Journal*, vol. 9, No. 11, pp. 3437–3445, 1990.

Raghaven, V., "mRNAs and a Cloned Histone Gene Are Differentially Expressed During Anther and Pollen Development in Rice", *Journal of Cell Science*, 92:217–229, 1989.

Reddy, A. S. N., et al., "Molecular Cloning of cDNAs for Auxin-Induced mRNAs and Developmental Expression of the Auxin-Inducible Genes", *Plant Molecular Biology*, 14:643–653, 1990.

Rommens, C., et al., "A Transposon Tagging Strategy With Ac on Plant Cell Level and Heterologous Plant Species", *Plant Science*, 74:99–106, 1991.

Schweinfest, C., et al., "Subtraction Hybridization cDNA Libraries from Colon Carcinoma and Hepatic Cancer", *Genet. Annal. Techn. Appl.*, 7:64–70, 1990.

Smith, A., et al., "Identification and Characterization of Stamen- and Tapetum-Specific Genes from Tomato", *Mol. Gen. Genet.*, 222:9–16, 1990.

Sommer, H., et al. "Deficiens, A Homeotic Gene Involved in the Control of Flower Morphogenesis in *Antirrhinum majus*: The Protein Shows Homology to Transcription Factors", *EMBO Journal*, vol. 9, No. 3, pp. 605–613, 1990.

Sotelo, J., et al., "Cloning, Sequence Analysis, and Expression of a cDNA Encoding a Plastid Localized Heat Shock Protein in Maize", *Plant Physiol.*, 93:1321–1328, 1990.

Twell, D., et al., "Isolation and Expression of an Anther-Specific Gene From Tomato", *Mol. Gen. Genet.*, 217:240–245, 1989.

Weiland, I., et al., "A Method for Difference Cloning: Gene Amplification Following Subtractive Hybridization", *Proc. Nat'l. Acad. Sci. USA*, vol. 87, pp. 2720–2724, Apr., 1990.

Yoder, J. I., et al., "Progress Towards Gene Targeting in Plants", *Genetic Engineering*, vol. 13 (Plenum Press, New York, 1991).

Frova, C., et al., (1987), "Isozyme and HSP Gene Expression During Male Gametophyte Development in Maize", *Isozymes: Current Topics in Biological and Medical Research*, vol. 15, Alan R. Liss, Inc., pp. 97–102.

Albertsen, M., et al., "Developmental Cytology of 13 Genetic Male Sterile Loci in Maize", *Can. J. Genet. Cytol.*, 23:195–208, 1981.

Doring, H. P., "Tagging Genes with Maize Transposable Elements. An Overview", *Maydica* 34 (1989): 73–88.

Rhodes, C., et al., "Genetically Transformed Maize Plants from Protoplasts", *Science*, vol. 240 (8 Apr. 1988).

Lyznik, L., et al., "Stable Co-Transformation of Maize Protoplasts with Gus A and Neo Genes", *Plant Molecular Biology*, 13: 151–161 (1989).

Wiegand, R., et al., "Messenger RNA Encoding a Glutahione-S-Transferase Responsible for Herbicide Tolerance in Maize is Induced in Response to Safener Treatment", *Plant Molecular Biology*, 7:235–243 (1986).

CONTROL OF MALE FERTILITY USING EXTERNALLY INDUCIBLE PROMOTER SEQUENCES

REFERENCE TO PRIOR APPLICATION

This application is a continuation-in-part of previously filed U.S. application Ser. No. 537,183, filed Jun. 12, 1990.

TECHNICAL FIELD

The present invention relates to the use of microsporogenesis genes and inducible promoters for the production of hybrid seed. In particular, it relates to regulating male sterility of such seed by controlling nucleic acid sequences affecting flavonol production.

BACKGROUND ART

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Maize plants (*Zea mays L.*) can be bred by both self-pollination and cross-pollination techniques. Maize has male flowers, located on the tassel, and female flowers, located on the ear, on the same plant. Natural pollination occurs in maize when wind blows pollen from the tassels to the silks that protrude from the tops of the incipient ears.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced. $F_1 \to F_2$; $F_2 \to F_3$; $F_3 \to F_4$; $F_4 \to F_5$, etc.

A hybrid maize variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid maize variety involves three steps: (1) the selection of superior plants from various germplasm pools; (2) the selfing of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeniety of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid, is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock. Likewise, it is very important in the production of hybrid seed to avoid self-pollination and the production and sale of inbred seed to end users.

Hybrid maize seed can be produced by manual detasseling. Alternate strips of two inbred varieties of maize are planted in a field, and the pollen-bearing tassels are removed from one of the inbreds (female). Providing that there is sufficient isolation from sources of foreign maize pollen, the ears of the detasseled inbred will be fertilized only with pollen from the other inbred (male), and the resulting seed is therefore hybrid and will form hybrid plants. Unfortunately, the manual detasseling process is not entirely reliable. Occasionally a female plant will be blown over by a storm and escape detasseling. Or, a detasseler will not completely remove the tassel of the plant. In either event, the female plant will successfully shed pollen and some female plants will be self-pollinated. This will result in seed of the female inbred being harvested along with the hybrid seed which is normally produced.

Alternatively, the female inbred can be mechanically detasseled. Mechanical detasseling is approximately as reliable as manual detasseling, but is faster and less costly. However, most detasseling machines produce more damage to the plants than manual detasseling. Thus, no form of detasseling is presently entirely satisfactory, and a need continues to exist for alternatives which further reduce production costs and the eliminate self-pollination in the production of hybrid seed.

The laborious detasseling process can be avoided by using cytoplasmic male-sterile (CMS) inbreds. Plants of a CMS inbred are male sterile as a result of cytoplasmic factors resulting from the cytoplasmic, as opposed to the nuclear, genome. Thus, this characteristic is inherited exclusively through the female parent, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown.

There can be other drawbacks to CMS. One is an historically observed association of a specific variant of CMS with susceptibility to certain crop diseases. This problem has led to virtual abandonment of use of that CMS variant in producing hybrid maize. In addition, CMS sometimes has a negative association with agronomic performance, particularly in the areas of stalk quality, early seedling vigor, and yield. Finally, CMS exhibits on occasion the potential for breakdown of sterility in certain environments, rendering CMS lines unreliable for hybrid seed production.

Another form of sterility, genic male sterility, is disclosed in U.S. Pat. Nos. 4,654,465 and 4,727,219 to Brat et al. However, this form of genetic male sterility requires maintenance of multiple mutant genes at separate locations within the genome and requires a complex marker system to track the genes and make use of the system convenient.

In self-pollinated species, such as soybeans and cotton, the male and female organs are anatomically juxtaposed. During natural pollination, pollen from the male reproductive organs of a given flower pollinate the female reproductive organs of the same flower. This is in contrast to cross-pollinated species, such as maize, where pollen from the tassel of one plant typically pollinates the silks of another plant through wind dispersal. This can readily occur because of the separation of the male and female reproductive organs. Hybrid production among self-pollinated crops can be difficult because of the close association of the male and female reproductive organs. In addition to the physical difficulty in effecting hybrid production in a self-pollinating crop, the amount of heterosis exhibited in a hybrid is often too low to justify the additional expense required to produce hybrid seed. A reliable form of male sterility would offer the opportunity for improved hybrid plant breeding and increased yields in these species.

Scientists have endeavored to understand development of pollen and the process of fertilization in maize and other plants. Fertilization begins with the germination of mature pollen on a stigmatic surface and the production of a tube which penetrates through the styler tissue. In angiosperms, the growing pollen tube is a conduit for transporting the two sperm cells to the embryo sac where they fuse with the egg and central cells to form the zygote and endosperm, respectively (E. G. Cutter, 1978, *Plant Anatomy, Part 1, Experimentation and Interpretation*, E. Arnold, Eds., Addison Wesley, London, Chap. 6). Pollen development takes place within the anther and at maturity each grain is a multi-celled spore containing products of both sporophytic gene expression, arising from the inner layer of the anther wall (tapetum), and haploid gene expression from the vegetative cell within each grain (J. P. Mascarenhas, 1990, *Annu. Rev. Plant Physiol. Plant Mol Biol.* 41:317; J. P. Mascarenhas, 1989, *Plant Cell* 1:657). Although the process of microsporogenesis is well documented histologically, little is known of the molecular and biochemical factors that are involved in post-dispersal pollen function.

Flavonoids are an abundant class of small molecular weight (~300) plant-specific metabolites which share a common 15 carbon skeletal structure. Modification of the basic structure yields an extensive array of compounds that are classified by the oxidation state and substitution pattern of the various rings. Some classes are pigments (e.g., anthocyanins, chalcones, and particular flavonols and flavones) while other classes are colorless ultraviolet-absorbing compounds. The anthocyanins, particularly pelargonin, cyanidin, and delphinidin, are responsible for the red, blue, and violet plant colors. Other pigmented flavonoids, the chalcones, and some flavonols and flavones are yellow and contribute significantly to the yellow, ivory and cream colored flowers. Pollen flavonoids have been identified in several species where they impact a distinctive yellow color to pollen and can account for a large percentage (2%–5%) of the dry weight (R. Zerbak, M. Bokel, H. Geiger, D. Hess, 1989, *Phytochemistry* 28;897; R. Wierinann and K. Vieth, 1983 *Protoplasma* 118;230). There is evidence that the pollen grain is a special environment for flavonoid biosynthesis and/or accumulation as several plant species have unique types of flavonoids in their pollen (O. Ceska and E. D. Styles, 1984, *Phytochemistry* 23:1822).

Plants having modified flavonoid pigmentation have been previously reported in the literature. For example, a maize mutant producing non-functional white rather than yellow pollen has been previously isolated and characterized (Coe E. H., McCormick S. M. and Modena S. A., 1981, "White Pollen in Maize," *J Hered* 72:318–320). The white pollen mutant sheds normal amounts of non-pigmented pollen which germinates on the silk, but no seed is set after most pollinations. The condition is sporophytically determined by the expression of stable recessive mutations at the two chalcone synthase (CHS) genes in maize, C2 and Whp. Recently, *Agrobacterium*-mediated introduction of a CHS transgene into a pigmented inbred petunia stock was reported to suppress the expression of the endogenous CHS gene(s), resulting in flower corollas completely lacking flavonoid pigmentation (Napoli C., Lemieux C. and Jorgensen R., 1990, "Introduction of a Chimeric Chalcone Synthase Gene Into Petunia Results in Reversible Co-repression of Homologous Genes in Trans," *Plant Cell* 2:279–289). CHS transgene is also suppressed in these plants, and the term co-suppression has been used to describe this phenomenon (Jorgensen R., 1990, "Altered Gene Expression in Plants Due to Trans Interactions Between Homologous Genes," *Trends Biotech* 8:340–344). The integrated transgene acts like an unlinked dominant inhibitor of the endogenous CHS gene(s) and leads to a complete block in the production of visible flavonoid pigments not only in flower petals but also reproductive organs.

Blockage of CHS gene expression not only results in flavonoid pigmentation deficiencies, but also in plants that are not fertile (Coe, et al., 1981; Taylor, et al., 1992, "Conditional Male Fertility in Chalcone Synthase Deficient Petunia", *J. Hered.*, 83:11–17). It would be highly desirable to be able to control fertility in a manner that plants may be effectively rendered male sterile or fertile as desired.

SUMMARY OF THE INVENTION

This invention relates to controllably rendering plants male sterile by using an inducible promoter to regulate expression of a gene critical to male fertilization such that the gene is normally "off" and the plant is thus sterile. When the promoter is induced, the plant becomes fertile. In particular, it relates to control of a gene affecting flavonol production in the plant.

It has now been discovered that plants in which flavonone-3-hydroxylase (F3H) activity has been impaired in a manner which produces a flavonol deficiency are conditionally male fertile (CMF), and that male fertility can be rescued or restored by providing conditions under which pollen of the plants may be contacted with fertility restoring flavonols. F3H activity may be impaired directly or indirectly, for example, by blocking F3H production in the plants, by inactivating F3H naturally produced by the plants or by impairing the activity of a precursor enzyme, such as chalcone synthase (CHS) in the flavonol biosynthetic pathway. Although viable pollen is produced by F3H deficient plants, pollen germination and tube growth are severely reduced both in vivo and in vitro, resulting in plants which are self sterile. However, by providing conditions under which pollen of the plant may be contacted with fertility restoring flavonols, full pollen germination and tube growth ability may be restored. Suitable fertility restoring conditions include any conditions where the required flavonols are made available to the pollen of the plants, including, for example, by removal of the F3H impairing condition, restoration of F3H production in the plants, and the like. Alternatively, fertility of the plants may be rescued or restored by contacting pollen of the plants with an amount of fertility restoring flavonol effective to enhance germination and/or tube growth of the pollen. Useful fertility restoring flavonols include compounds of the formula:

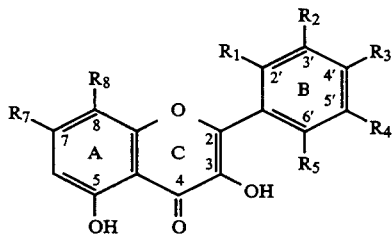

wherein $R_1$, $R_2$, $R_3$, $R_4$, $R_5$, $R_7$, and $R_8$, are hydrogen, hydroxyl or alkoxy having from 1 to 3 carbon atoms. Particularly, preferred flavonols include galangin, kaempferol, iso-rhamnetin, quercetin and morin.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3A shows whole anther sections immediately before dehiscence when CHS-deficient anthers are tan and shrunken. The bar in FIG. 3A represents 200 μm. FIG. 3B shows anther sections 48 hours before dehiscence when transgenic anthers are plump and white. FIG. 3C shows anther sections as FIG. 3A at the magnification of the representations of FIG. 3B. The bar in FIG. 3B represents 50 μm. FIG. 3D shows mature pollen at dehiscence. In FIGS. 3A, 3B, 3C and 3D, represents pollen; E, endothecium; S, stomium; and C, cuticle.

DISCLOSURE OF THE INVENTION

Figure 1:
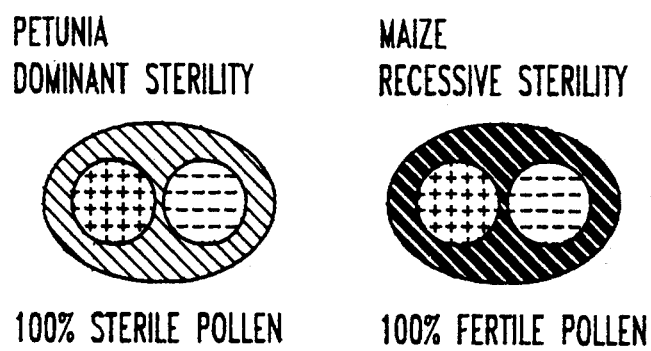
FIG. 1 is a schematic representation of sporophytic influence (diagonal lines) on the developing microspores in chalcone synthase (CHS) heterozygous plants. The lack of CHS function in the sporophyte is indicated by a white back ground and the presence of CHS function is represented by a black background.
Figure 6:
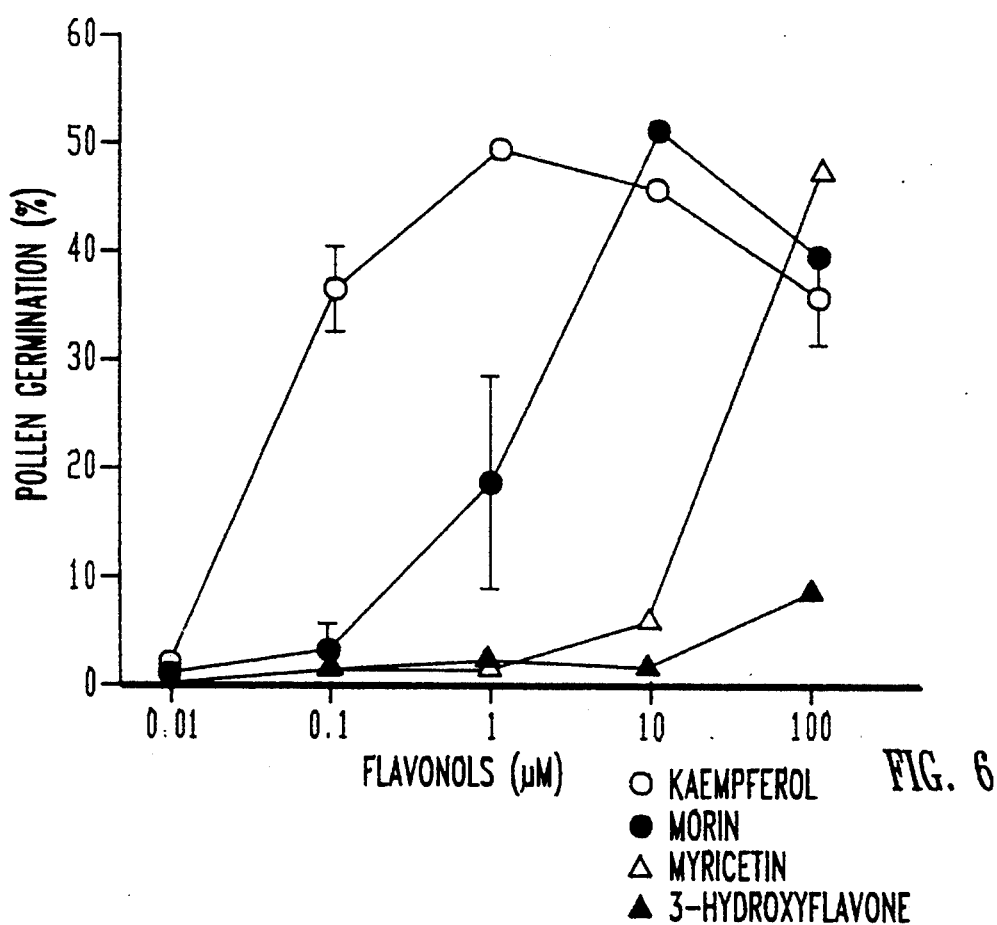
FIG. 6 is a graphical representation of pollen germination frequency as a function of increasing flavonol aglycone concentration, in which kaempferol (open circles), morin (closed circles), myricetin (open triangles) and 3-hydroxy-flavone (closed triangles) were added to germinating medium (GM) at the indicated final concentrations and germination was scored after 4 hours of incubation. The mean germination frequency measured in three separate experiments is plotted with the standard error of the mean (SEM). SEM values <1.4 are not visible. The germination frequency of the wild type control V26 pollen is typically 75% and the non-rescued DMSO-treated CMF pollen yields between 1-2% pollination.

All references referred to are incorporated herein by reference.

The present invention differs from conventional approaches to male sterility in plant breeding and seed production in that an inducible promoter is used to regulate expression of a gene which is known to be critical in microsporogenesis, i.e., the production of pollen. The first step in the practice of this invention is therefore the selection of a gene on which microsporogenesis is dependent. One of the types of genes found critical to microsporogenesis are those affecting flavonol production.

The selected gene is cloned, its native promoter enabled, and the modified gene is inserted into an expression sequence with an inducible promoter responsive to external control. Preferably, the promoter is one which responds to application of a specific non-phytotoxic chemical to the plant.

Using transformation and gene substitution, the "critical" gene is inactivated in the genome of the plant and replaced by the genetically-engineered gene incorporated into the expression sequence with the inducible promoter.

This invention is unique in that the inducible promoter is used to induce fertility, not sterility. In this invention, the selected gene's promoter sequences are removed so that the gene is not transcribed and the plant is male sterile. When it is desired to increase the male-sterile plant, male fertility is restored by inducing expression of the critical gene. In the preferred embodiment this is accomplished by treating growing male sterile plants with a specific non-phytotoxic chemical.

It will be appreciated that male sterility could be imparted in a manner by which the "critical gene" is "off" and requires the chemical for expression, or in a manner by which the critical gene is "on" and chemical treatment is necessary to impart sterility. The latter method is described in PCT Publication W089/10396 of Mariani et al., (based on Intl. Appl. No. PCT/EP89/00495) incorporated herein by reference.

Induction of the inducible promoter by chemical treatment will be dependent on various factors associated with the chemical treatment itself and various environmental conditions at the time of treatment. If the critical gene were normally "on," to be inactivated by chemical treatment, a treatment failure would result in self-pollination and production and sale of inbred, rather than hybrid seed. Seed laws that govern the sale of hybrid seed require a high degree of seed purity such that percentages of seed that do not conform to the hybrid specification must be kept very low. Because one maize plant can produce in excess of six million pollen granules, even a limited treatment failure could result in a high percentage of self-pollination. For these reasons, the present invention is practiced in such a manner that the gene is normally "off" and the corresponding trait is not expressed, so that under normal conditions self-pollination cannot occur. In addition, by having the critical gene normally "off," chemical treatment is not necessary in the large-scale production of hybrid seed, so that chemical usage (and associated expense) is minimized and the risk of treatment failure is present only in the carefully controlled, limited scale production of parent seed, where self-pollination is desired. Since treatment failure in such a case results in underproduction of pollen, and since pollen is normally overproduced by a wide margin, the process of this invention for production of parent seed will tolerate a treatment failure rate as high as 70% to 80% with minimal effects on yield of parent seed.

INDUSTRIAL APPLICABILITY

Identifying Genes Critical To Male Fertility

The procedures for identifying and cloning a male sterile gene are the same as those known in the art to be utilized to clone other genes. The preferred method is transposon (transposable element) tagging because most instances of genetic male sterility in maize are the result of recessive gene mutations. Cloning techniques that require knowledge of the protein sequences of a male sterile gene translation product cannot be used at present because the gene product of male sterile genes is not yet known.

The procedure for tagging maize genes with transposable elements is known, as reviewed by H. P. Doring, "Tagging Genes with Maize Transposable Elements. An Overview". Maydica 34 (1989): 73–88 and described in U.S. Pat. No. 4,732,856 to Federoff ("Transposable Elements and Process for Using Same"), the disclosures of which are incorporated herein in their entirety.

One of the methods by which this is carried out is by intercrossing a maize strain carrying active transposable elements and a dominant allele of the target gene involved in microsporogenesis with a normal maize strain that does not carry transposable elements. Specific gene tagging efficiency can be and preferably is enhanced by positioning the transposable element in the proximity of the target gene locus. Progeny from the intercrosses are selfed and subsequently screened for the most useful mutations. The preferred phenotypes are plants which do not extrude anthers and those which do not produce pollen. Most preferred are phenotypes which do not extrude anthers because this phenotype can easily be screened visually prior to pollination time by gross observation. These male sterile plants represent putative instances in which a transposable element has excised from its original location and has transposed to a locus bearing a gene which is essential for pollen development. Once the transposable element has transposed to such a locus, the gene is inactivated. It will then behave as a recessive gene and result in male sterility. These mutant plants can be crossed to tester stocks for the transposable element to confirm that the element is still present.

Once it has been confirmed that the desired transposable element has transposed into the target gene, genomic clones which hybridize to the transposable element are constructed. The element adjacent sequences of the clones are then used as probes in Southern hybridizations with genomic DNA from strains carrying the mutant allele, the revertant allele, and the wild-type allele. The rDNA which reveals the expected differences in size (reflecting the presence or absence of the transposable element) carries the desired modified target gene.

In practice, the frequency with which a particular locus can be targeted with a transposable element usually varies from $10^{-5}$ to $10^{-6}$. However, 100,000 maize plants can easily be grown on an area of less than 10 acres. In addition, under certain circumstances the frequency of the element-induced mutations can be increased. For example, the particular transposable element to be used for gene tagging can be linked to the gene to be tagged by the element. For two different transposable element systems, Ac and Spm/En, the transpositions of these elements occurs preferentially to sites on the chromosome where the element was located before the transposition. Alternatively, different transposable elements have different frequencies of mutation induction. For example, the transposable element called Mutator (Mu) is able to induce new mutations at a frequency 30 to 50 times higher than the frequency in control plants. Additionally, the rate of mutation induction can be influenced by the sex of the element carrying parent. While it cannot be predicted which of the reciprocal crosses will give the higher mutation rate, transposon tagging can readily be performed.

At least seven different maize transposable elements have been cloned at this time. These are Ac, Spm/En, Mu, Tz86, Bs1, rDt, and Mpil. Any of these can be used to clone genes in which a transposable element resides.

One skilled in the art will appreciate this is but one example of means to locate such genes and that other methods are well known.

One collection of mutant genes is already known, and has been described by Albertsen, et al. "Developmental Cytology of 13 Genetic Male Sterile Loci in Maize". Can. J. Genet. Cytol. 23: 195–208, 1981, incorporated herein by reference. These are known as male-sterile (ms) genes. These genes affect development of the pollen only; they have no effect on female organ development. These genes disrupt microsporogenesis at characteristic stages of pollen development, rendering the plant male sterile.

Once the mutant gene from any of the foregoing sources has been cloned, it is used as a probe to clone the wild type allele. This is possible because the mutated gene is very closely similar to the wild type allele, and as such, hybridizes to the wild type allele. Once the normal gene has been identified and cloned, the region of the gene known as a promoter region is identified. This region is involved in the start of transcription of that gene.

Genes which are essential to pollen development can also be identified without intermediate use of mutations by isolating mRNA's that are uniquely present during pollen development and constructing a cDNA that can be used to probe a genomic library for the corresponding gene.

The surprising discovery has further been made that flavonol, and in particular, certain flavonols, are critical to pollen function, and that their production or lack thereof can control fertility and sterility.

Plant fertility in a flavonoid-deficient, conditionally male fertile (CMF) plant is restored by contacting pollen of the plant with fertility restoring flavonols effective to enhance germination of the pollen of the plant. In an illustrative example, suitable conditions may be obtained by contacting pollen of the plant with an amount of a fertility restoring flavonol effective to enhance germination and tube growth of the pollen of the plant. As used herein, the term flavonoid-deficient, conditionally male fertile or CMF plant is intended to include plants in which the chalcone synthase (CHS) or flavonone-3-hydroxylase (F3H) activity has been impaired, either naturally or transgenetically, to disrupt the natural production of flavonoids in the plant. Accordingly, flavonoid-deficient, conditionally male fertile plants will typically be pigment deficient, resulting in a white or pale coloration, and will typically be self sterile. Although the invention will be hereinafter described in detail in connection with CMF petunias and maize, other CMF plants may be similarly used in the practice of the invention.

In the natural flavonol biosynthetic pathway, chalcone synthase (CHS) condenses three molecules of malonyl-CoA and one molecule of p-coumaroyl to form chalcononaringenin, which is converted to naringenin spontaneously (at a low rate) and by the action of chalcone-flavanone isomerase (CHI). In the next step of the pathway, F3H catalyzes the addition of a hydroxyl group to the 3-position carbon of the C ring to produce a flavonol, which is required for fertility restoring activity in accordance with the present invention. The general pathway may be represented as follows:

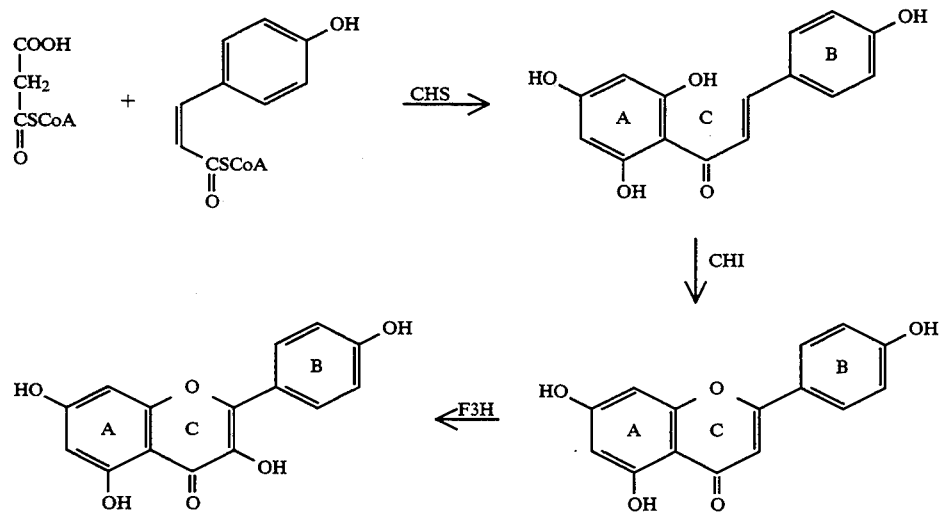

F3H is the rate limiting enzyme in the production of flavonols, and has been previously cloned from *Antirrhinum majus* (Martin, C., Prescott, A., Mackay, S., Bartlett, J. and Vrijlandt, E., 1991, "Control of Biosynthesis in Flowers of *Antirrhinum magus*," The Plant J., 1:37–39). Since flavonol aglycone compounds are required for male fertility, as described here, an inducible promoter controlling the F3H hydroxlation activity may be employed in the practice of the invention.

Impairment of male function in plants which lack flavonoids as a result of a deficiency in CHS, CHI or F3H activities result in no gross abnormalities in pollen development until immediately prior to dehiscence when the anther morphology deviates from normal in color, shape, and size. At dehiscence the pollen remains clumped within the anther and when viewed microscopically a significant proportion of the grains in a locule appear more shrunken than normal. Although viable pollen is produced and shed, pollen germination and tube growth are greatly impaired both in vivo and in vitro. In addition to functional male sterility, flavonol-deficient plants exhibit some aspects of self-incompatibility, as evidenced by the fact that the pollen can be partially rescued by stigmas of wild type plants, but not by stigmas of flavonol-deficient plants. Although elements of both male sterility and self incompatibility are evident, the features exhibited by pollen from the flavonol-deficient plants clearly constitute a unique state which is referred to herein as conditional male fertility (CMF).

Plants lacking CHS (and therefore lacking flavonoids) appear normal except for two features: (1) a lack of flavonoid pigmentation and (2) the production of impaired pollen that is entirely dependent on wild pistils (stigma+style) in order to function.

While CHS deficient plants share a lack of flavonoid pigmentation and pollen function impairment, some differences are evident between plant species. Maize white pollen germinates on the silks and produces a pollen tube whose growth is arrested in the style. Additionally, the maize mutant pollen germinates in vitro and produces a tube nearly as long as wild-type pollen. In contrast, pollen from the CHS-deficient petunia does not penetrate the stigma nor produce a tube either in vivo or in vitro. This difference between maize and petunia may be explicable in terms of the physiological differences between tricellular (maize) and bicellular (petunia) pollen. Bicellular pollen has a low respiratory rate when shed, forms the second sperm cell after shedding, may be on the sigma several hours before germination and has a low initial pollen tube growth rate. Tricellular pollen, by comparison, undergoes the second mitotic division before anthesis, has a high respiratory rate when shed, germinates within minutes after contact with the stigmatic surface and has a high initial growth rate. Because tricellular pollen is poised to grow rapidly after shedding, maize white pollen tubes grow to a significant length before any mechanism that arrests tube growth is effective.

In flowering plants with alternating generations, the diploid sporophyte produces haploid spores which grow and divide mitotically to produce the gametophyte. Part of the gametophytic life cycle occurs while the developing pollen spore is in intimate contact with surrounding sporophytic tissue. This arrangement has the potential for diploid-haploid interactions. In heterozygous plants this interaction would also include haploid-haploid communication between the two types of gametophytes as represented in FIG. 1. The fact that the petunia flavonoid-deficient male sterility described here is genetically dominant while the maize white pollen male sterility is genetically recessive leads to an interesting conclusion regarding whether the gametophyte or the sporophyte is responsible for the effect. In maize, male sterility is expressed only in plants homozygous recessive for both CHS genes, c2 and Whp. Heterozygotes with either a single functional copy of C2 or Whp produce 100% yellow, fertile pollen grains (Coe, et al. 1981). Thus, in the heterozygote either the CHS-positive sporophyte or the 50% CHS-positive gametophytes influence the expression of fertility in the CHS-negative gametophytes. In the transgenic petunia, male sterility is associated with a dominant trait and pollen produced by the heterozygous plants is 100% male sterile. In this case, sterility is caused either by inhibition of the CHS-positive gametophytes by the CHS suppressed gametophytes or by CHS deficiency in the transgenic sporophyte (FIG. 1). The physiological basis for CHS deficiencies causing male sterility appears to be the same in maize and petunia, and in both species it is the sporophyte that causes the sterile phenotype, rather than the gametophyte. Thus, the conditional male fertility associated with CHS deficiency in maize and petunia has a common physiological basis.

Control of fertility by regulation of flavonol production is evident by the fact it has been found it is possible to exploit the production of conditionally sterile pollen from the CHS-deficient plants to form the basis of an in vitro pollen rescue assay. By incubating the transgenic pollen in germination solution supplemented with purified flavonoids or plant extracts and assaying for enhanced germination frequency and pollen tube growth, specific compounds required for pollen function can be identified. In this manner, it has been determined that the broad family of flavonoid compounds, in general, is not uniformly effective in restoring fertility in CMF plants, but rather that a specific group of fertility restoring flavonol aglycones is effective for this purpose.

Any flavonol which is effective in promoting germination of pollen of a CMF plant may be used in the practice of the invention. It has been found, however, that most members of the relatively large family of flavonoids are ineffective for this purpose. Particular effective fertility restoring flavonols can be identified and used in the restoration of plant fertility in a CMF self sterile condition. In a preferred embodiment of the invention, the fertility restoring flavonol is a compound of the formula:

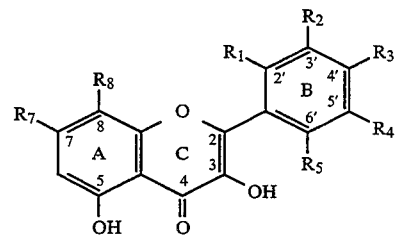

wherein $R_1$, $R_2$, $R_3$, $R_4$, $R_5$, $R_7$, and $R_8$, are hydrogen, hydroxyl or alkoxy having from 1 to 3 carbon atoms. More preferably, not more than two of $R_1$–$R_5$ are hydroxyl or methoxy and the remaining $R_1$–$R_5$ are hydrogen, and $R_7$ and $R_8$ are hydrogen, hydroxyl or methoxy. Presently particularly preferred and representative fertility restoring flavonol compounds of the invention include galangin, kaempferol, iso-rhamnetin, quercetin, and morin which have the general chemical structure set forth above with the following substituents:

TABLE 1

| Flavonol | $R_1$ | $R_2$ | $R_3$ | $R_4$ | $R_5$ | $R_6$ | $R_7$ |
|---|---|---|---|---|---|---|---|
| galangin | H | H | H | H | H | OH | H |

TABLE 1-continued

| Flavonol | $R_1$ | $R_2$ | $R_3$ | $R_4$ | $R_5$ | $R_6$ | $R_7$ |
|---|---|---|---|---|---|---|---|
| kaempferol | H | H | OH | H | H | OH | H |
| Iso-rhamnetin | H | OCH$_3$ | OH | H | H | OH | H |
| quercetin | H | OH | OH | H | H | OH | H |
| morin | OH | H | OH | H | H | OH | H |

Other flavonols useful in the practice of the invention may be readily determined using the in vitro pollen rescue assay methods set forth herein.

The foregoing may be better understood in connection with the following examples, which are presented for purposes of illustration and not by way of limitation.

EXAMPLE 1

Fertility of Chalcone Synthase-deficient Petunias

Transgenic and inbred V26 petunia were maintained on a 16/8 hour photoperiod in a glasshouse supplemented with metal halide lights at an intensity of 300–600 $\mu$mol m$^{-2}$sec$^{-1}$. Inbred V26 is a pigmented line of Petunia hybrids which can produce flavonoids in most plant tissues including pollen, anthers and filaments, and pistil (stigma+style) and is fully self-compatible. The transgenic material analyzed consisted of the two independent transformed regenerants, 218.38 and 218.41 (Napoli C., Lemieux C. and Jorgensen R., 1990, "Introduction of a Chimetic Chalcone Synthase Gene Into Petunia Results in Reversible Corepression of Homologous Genes In Trans," *Plant Cell* 2:279–289) and individuals from the second backcross generations (BC2) to the parental V26 line (population numbers 2425 through 2435). The T-DNA insertion in theses transformants contains CHS cDNA sequences fused to a viral promoter linked to a neomycin phosphotransferase II gene as a selectable marker (Napoli et al. 1990). Crosses were performed by emasculating flowers 24 hours prior to the application of pollen. All transgenic flowers used for crosses showed no visible signs of pigment. Pollen donors were selected from plants that had 2 to 3 dehiscent anthers or dissected from plump, pre-dehiscent anthers as noted.

The transgenic petunia plants 218.38 and 218.41 where pure white flowers after the introduction of an additional copy of the CHS gene. When CHS expression was examined in the transgenic petals, a 50-fold induction in mRNA compared to the untransformed V26 parent or somatic revertants was detected in both endogenous and introduced CHS genes. The V26 inbred line produces purple anthocyanin pigments in leaves, stems, pedicles, styles and anther filaments, and yellow chalcones in developing anthers. In comparison, the transformed plants have no discernible flavonoid pigments in any of these tissues. The lack of visible pigment has ben confirmed by HPLC analysis of methanolic extracts as described in Example 6. Normally, just prior to shedding, petunia anthers filled with mature pollen undergo desiccation. At dehiscence, when the anther case ruptures longitudinally along the stomium, the dehydrated state of the tissue results in the two edges of the anther lobe curling back on one another to expose the pollen grains. Close inspection of the non-pigmented transgenic plants reveals that, in the 48 hours preceding dehiscence, the anthers shrink an average of 40% in length and change in color from creamy-white to tan. In comparison, the anthers of the non-transformed parental line V26 shrink only about 15% and do not undergo a color change, remaining yellow throughout this period. A wide variation in the frequency of dehiscent anthers occurs ranging from 0 to 100% with the higher frequency associated with lowered relative humidity. Although dehiscence may be slightly delayed relative to the V26 parent, the CHS-deficient anthers do open to expose normal amounts of pollen which does not appear as light and friable as V26 pollen and remains clumped within the anther case.

No seeds resulted from numerous attempts at self pollination of the flavonoid-deficient progeny of 218.41 using either: (i) pollen from shrunken, tan, dehiscent anthers or (ii) pollen dissected from white, plump, pre-dehiscent anthers (see Table 2, column 5, "Transgenic Self Crosses: 0 seeds/pod"). Self crosses of the V26 parent line produce on average 225 seeds per pod. This translates to approximately 17,000 possible seeds in the 75 transgenic petunia self crosses that were attempted. All of the plants listed in Table 2 were tested for female fertility by pollinating stigmas with pollen from inbred line V26. In all cases, pods were produced with the normal complement of seeds, indicating that the CHS-deficient plants are female fertile. The reciprocal cross, transgenic flavonoid-deficient pollen onto V26 stigmas resulted in the production of varying quantities of seeds as shown in Table 2.

TABLE 2

Seed Production From Transgenic Pollen Crosses
NUMBER OF POLLINATIONS

| Pollen Parents | V26 × transgenic pollen | | | Transgenic self crosses 0 seeds/pod |
|---|---|---|---|---|
| | 0 seeds/pod | 1–150 seeds/pod | >150 seeds/pod | |
| 02425.1* | 0 | 2 | 0 | 8 |
| 02430.5 | 0 | 5 | 3 | 6 |
| 02430.6 | 2 | 1 | 0 | 6 |
| 02430.8 | ND | ND | ND | 6 |
| 02432.2 | ND | ND | ND | 6 |
| 02435.1 | 0 | 1 | 1 | 6 |
| 02435.2 | 1 | 4 | 1 | 8 |
| 02435.3 | 0 | 1 | 1 | 7 |
| J2425.1* | 0 | 1 | 0 | 1 |
| J2428.1 | ND | ND | ND | 6 |
| J2431.2 | 2 | 3 | 0 | 6 |
| J2432.3* | 3 | 0 | 0 | 7 |
| J2430.5* | 3 | 2 | 0 | 2 |

*Flowers on other branches of this plant had some purple pigment in corolla.
$^a$At least 4 flowers on each plant listed was pollinated with V26 pollen and all set full seed pods.
Average number will/pod = 225.

Of 37 crosses involving 10 different transgenic plants as male parents, 11 produced no pods, 20 produced pods with less than 150 seeds per pod and 6 produced pods with greater than 150 seeds per pod. This averages to approximately 60 seeds per pod or a 70% reduction in seed set. These results indicate that while pollen from the flavonoid-deficient plants is non-functional on flavonoid-deficient stigmas it is partially functional on wild type stigmas, the state we termed herein as conditional male fertility (CMF). The wide variation in the number of seeds set per pollination in these outcrosses is possibly due to environmental and/or developmental factors.

It is unlikely that CMF is due to the insertion of T-DNA into a gene required for male fertility since two independent transformants, 218.38 and 218.41, both display the same features: a complete lack of flavonoid pigmentation and identical dominant male sterile phenotypes. Additional evidence for this conclusion comes from the observations of Napoli et al. (1990) that the transformed regenerants sometimes revert somatically to fiery pigmented plants but retained the transgene, indicating that the presence of the transgene alone does not suppress endogenous CHS expression.

Given the similarity with white pollen in maize, CMF in petunia appears to be caused by a deficiency in flavonoids, such as that caused by a suppression of CHS or F3H gene expression.

EXAMPLE 2

Pollen Germination and Tube Growth

In vitro germination was performed on freshly collected pollen in simplified Brewbakers medium as described in Mulcahy GB and Mulcahy DL, 1988, "The Effect of Supplemented Media on The Growth in vitro of Bi- and Trinucleate Pollen," *Plant Science* 55:213–216 (herein sometimes referred to as "germinating medium" or "GM"). Pollen from a single anther was placed in a microtiter well with 50 $\mu$l of media, rocked at room temperature for 6 to 8 hours and photographed with Kodak technical pan film.

In vivo pollen tube growth was measured 48 hours post-pollination as described in Herrero M. and Dickinson H. G., 1979, "Pollen-pistil Incompatibility in Petunia Hybrids: Changes in the Pistile Following Compatible and Incompatible Intraspecific Crosses," J. Cell Sci, 36:1–18. Callose plugs were visualized by epifluorescence generated by excitation at 355–425 mn (D cube) and suppressing wavelength 460 nm from a Leitz Aristoplan. Specimens were photographed with Ektrachrome T 160 film and prints made from an internegative.

Pollen viability was determined with the fluorochromatic procedure (FCR) (Heslop-Harrison J. and Heslop-Harrison Y. 1970, "Evaluation of Pollen Viability by Enzymatically Induced Fluorescence; Intracellular Hydrolysis of Fluorescein Diacetate," Stain Technol 45:115–120) by incubating freshly dehiscent pollen in a solution of carboxyfluoresceine acetate (1 mM) in germination media. Epifluorescence was visualized as described above.

Callose Production

Petunia pollen tubes normally penetrate the stigma about one hour after germination (Herrero and Dickinson 1980) and grow downward through the styler tissue to deposit the two sperm cells in the embryo sac. Callose is a polysaccharide polymer-linked in $\beta$(1–3) glycosidic linkages and plugs of this material are normally deposited at regular intervals down the growing pollen tube. Callose is visualized by its distinctive fluorescence after staining with decolorized aniline blue (Currier 1957; Eschrich and Currier 1964). The germination and growth of pollen tubes in self crosses of CHS-deficient flowers and in backcrosses of the same plants with V26 pollen were examined. Pistils were harvested 48 hours after pollination, stained with decolorized aniline blue and examined by fluorescent microscopy. A regular pattern of callose deposits was observed all the way down the style in the squashes of flavonoid-deficient pistils pollinated by V26. On the other hand, no callose was seen in the pistils of the self pollinated petunias even though copious amounts of pollen was present on the stigma.

Pollen Morphology and Germination

Figure 2A:
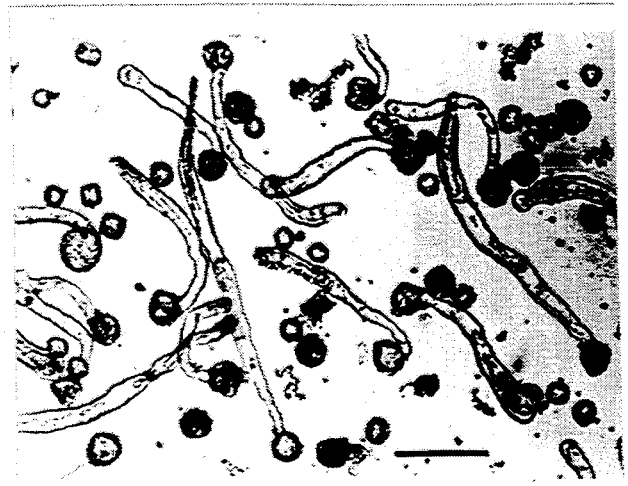
FIGS. 2A and 2B are photographic representations of in vitro germinating pollen from inbred petunia line V26 (FIG. 2A) and CHS-deficient plant 02425.1, wherein the pollen from freshly dehiscent anthers was suspended in a liquid medium and photographed after growth at room temperature for 6 hours. The bar in FIG. 2A represents 25 μm. The arrows in FIG. 2B indicate pollen tubes attempting to germinate.
Figure 2B:
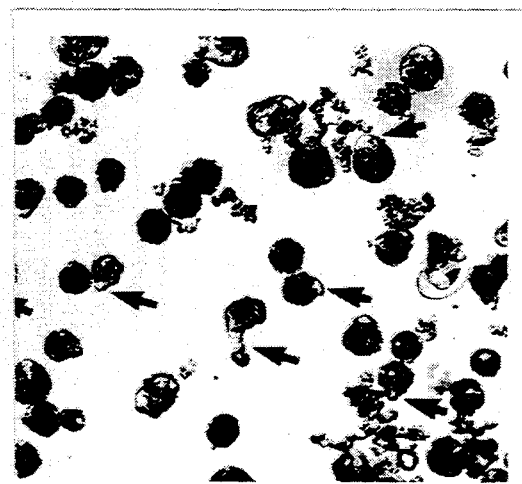

A microscopic examination of freshly shed pollen from flavonoid-deficient plants of Example 1 was made and did not reveal any gross abnormalities. Petunia pollen readily germinates and produces a tube when incubated in a simple liquid medium. Germinated pollen from each of the BC2 families (2425 to 2435) to V26 pollen were compared in vitro. A typical representative is shown in FIG. 2. As shown, after 6 hours of growth many mutant pollen grains have attempted germination as noted by the pronounced swelling around one of the germination pores (arrows, FIG. 2), but at most only 2% of the pollen grains from the CHS-deficient plants produce a tube of any length. Of the pollen grains that do produce measurable tubes, the length is less than 20% of the length of V26 pollen tubes grown under identical conditions.

To determine whether the pollen produced and shed by the flavonoid-deficient plants was viable and therefore capable of germination and pollen tube growth, a fluorochromatic analysis (FCR) for viability on freshly shed transgenic and V26 pollen was performed. This test depends on the uptake of a fluorescein diacetate compound into the pollen grain with subsequent conversion to fluorescein by intracellular enzymes. Fluorescein is highly polar and remains sequestered, most likely in the vegetative cell cytoplasm, where it is visualized by fluorescent microscopy. Inbred V26 pollen consists of a high proportion (up to 40%) of abnormally small, FCR negative grains which entirely lack any internal features. Several grains of this type can be seen in FIG. 2A, including two in the center of the photograph. This population never germinates and is most likely aborted grains. Of the remaining grains (60%), almost all showed a positive FCR test, indicating the presence of intact plasma membranes and active cytoplasmic esterases. Pollen from the mutant anthers retains the high proportion of shrunken, aborted grains. Of the remaining normal appearing grains, more than 90% were FCR positive. The fact that most of the pollen produced by the flavonoid-deficient plants was viable and metabolically active indicates that some aspect of flavonoid activity is required for normal pollen germination and tube growth.

EXAMPLE 3

Microscopic Observations of Anther Development

Figure 3A:
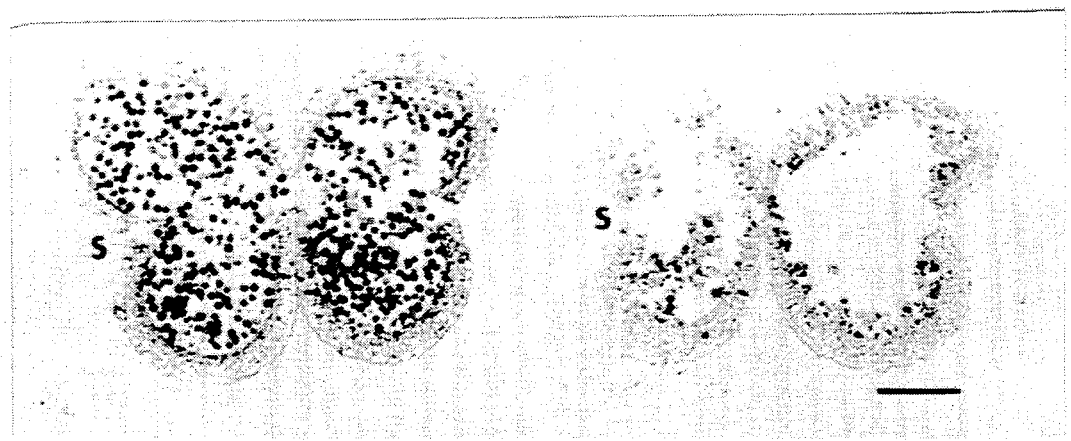
FIGS. 3A, 3B, 3C and 3D are photographic representations of cross sections of developmentally identical anthers from inbred petunia line V26 (left column) and from CHS-deficient plant 025425.1 (right column), which had been harvested, fixed, embedded, transversely sectioned and stained with toluidine blue as described in Example 3.
Figure 3B:
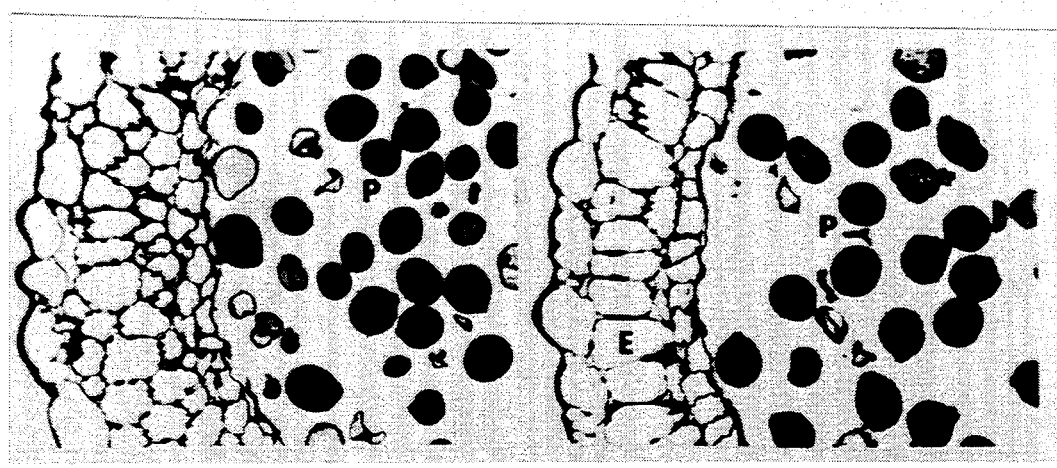
Figure 3C:
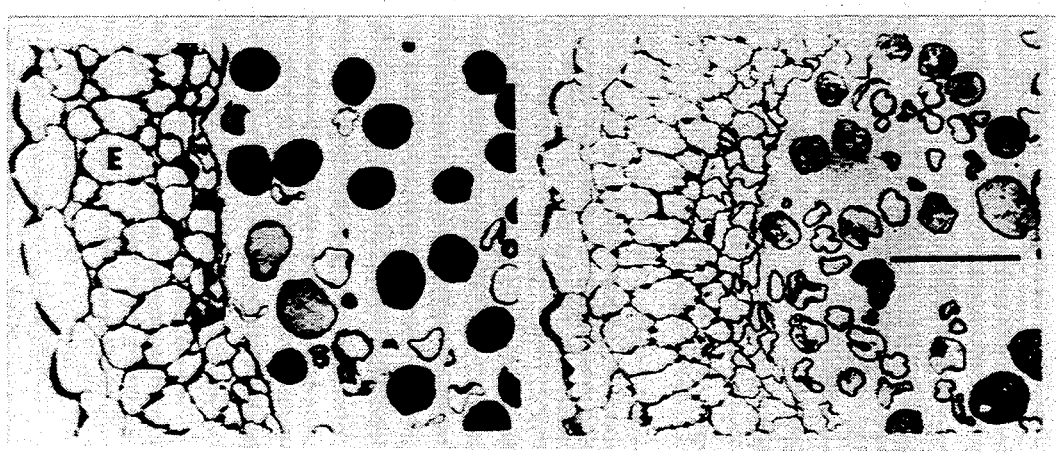
Figure 3D:
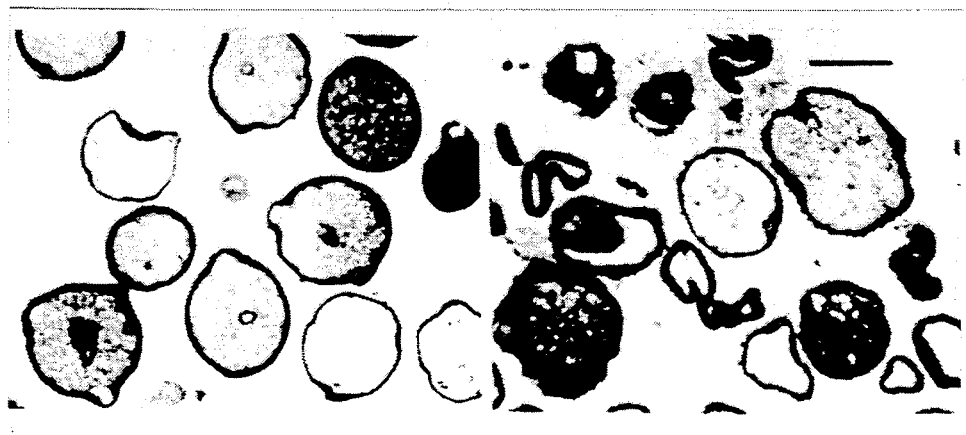

To determine if the lack of flavonoid activity during microsporogenesis altered the cellular architecture of the developing pollen grains or anther tissues, pollen development in V26 and flavonoid-deficient plant 02425.1 was compared. Anthers from a developmentally staged series of petunia buds ranging in length from 0.1 to 6 cm. were harvested, fixed in 2% paraformaldehyde, 1.25% gluteraldehyde in Pipes, pH 7.Z embedded in Spurts resin and 1 $\mu$m sections were stained with toluidine blue. Photomicrographs were made with Kodak technical pan film. Histologically this represents all stages of microsporogenesis, from the earliest evidence of archesporial tissue differentiation to pre-dehiscent anthers filled with mature pollen. Close attention was given to the development and subsequent disintegration of the tapetum, since this tissue is thought to be the source of pollen flavonoids. At all stages the transgenic anther and developing microspores showed no gross histological differences when compared to V26. Additional sections were taken from the flavonoid-deficient anthers during the transition from plump, white to shrunken, tan and compared to similar stages in V26 (FIG. 3). Preceding dehiscence the cells of the endothelial layer normally expand radially, thicken, and deposit material which is thought to be involved in the mechanism of anther rupture (Cutter, E. G., 1978, "Plant Anatomy: Experimentation and Interpretation, Part I", *Cells and Tissues*, 2nd Ed., Landon: Arnold). This layer is not continuous, being absent in the area surrounding the stomium. The sections of the shrunken, tan anthers show no gross abnormalities to the endothelial layer, stomium, or cuticle surrounding the anther. However, when compared to V26 pollen (FIG. 3, Column "V26") a higher proportion of shrunken grains devoid of internal features were present in the locules of the transgenic plants and the larger grains appeared more heterogeneous in size, shape, and staining reaction (FIGS. 3C and 3D). The heterogeneity shown in FIGS. 3C and 3D may be accounted for by the fact that pollen is normally shed in a highly dehydrated state and undergoes rapid rehydration on the stigma flavonoid-deficient pollen may be shed in a much more dehydrated state than normal, and when placed in liquid germination medium, appears to rehydrate to a normal appearance.

EXAMPLE 4

Petunia Flavonoid Extracts

Analyses of petunia pollen extracts have identified the major flavonoids as 3-0-glycosides of quercetin and kaempferol, 4,2', 4', 6'-tetrahydroxychalcone, and a dihydroflavonol, taxifolin (Zerback, R., Bokel, M., Gieger, H. and Hess, D., 1989, *Phytochemistry* 28:897–899; Zerback, R., Dressier, K. and Hess, D., 1989, *Plant Science* 62:83–91; De Vlaming, P. and Koh, K. F .F., 1976, *Phytochemistry* 15:348–349). Maize pollen contains at least 10 glycosides of kaempferol, quercetin, and isorhamnetin (Ceska, O. and Styles, E. D., *Phytochemistry* 23:1822–1823). Aqueous extractions from both wild type and inbred petunia line V26 were made by macerating stigmas with forceps or vortexing a pollen suspension in PEG 4000 media (W. Jahnen, W. M. Lush, A. E. Clarke, 1989, *Plant Cell* 1:501), hereafter referred to as GM, centrifuging 5 min in a microfuge, and applying aliquots of the supernatant directly to a CMF pollen suspension in GM in a 96 well microtiter plate. Methanol extraction followed the same protocol except the extract was dried under vacuum and resuspended in GM before addition to the pollen suspension. The initial rescue experiment elicited a 33% germination rate using 20 $\mu$l (one-fifth total volume) of an aqueous extract prepared from ten V26 stigmas. As a control, extracts were prepared in a similar manner from stigmas and pollen of the CMF plants. In pollen germination assays only extracts from V26 stigmas and pollen were able to restore germination and tube growth to the flavonoid-deficient pollen.

The wild type and CMF pollen and stigma extracts were analyzed as follows. Stigmas or pollen were extracted first with 50% methanol, followed by 100% methanol, and the extracts were pooled and concentrated. Aglycones were produced by acid hydrolysis: the extract was mixed v/v with 4N HCl sealed in a 2 ml ampule and hydrolyzed in boiling water for 40 min. Replicate samples were injected into a reverse-phase C18 column (Phenomenex Spherisorb 5 ODS 2 250×4.6 mm). Solvent A was 5% acetic acid and solvent B consisted of 5% acetic acid in 80% acetonitrile. Each run consisted of a 6 min isocratic gradient (20%B), followed by a 20 min linear gradient to 90% B and terminated isocratically at 95% B for 14 min. The solvent flow rate was 0.5 ml/min at room temperature. Detection was at 360 nm with a Hewlett Packard Model 1040A photodiode array detector. Kaempferol was detected in the wild type stigma extracts at 60 ng sigma, and quercetin at substantially lower levels. Identical extracts from a pool of 150 CMF stigmas or from 500 CMF anthers yielded no peaks giving a typical flavonol spectra.

Treatment of the wild type stigmatic extract with protein digesting enzymes, heat, and passage through molecular sizing membranes indicated that the active compound was a small non-proteinaceous molecule. The molecular weight of the active compound was estimated by passing the extract through a 3000 dalton molecular weight cutoff filter (Centricon-30 filter, Amicon) and establishing that the pollen rescue activity passed through the filter. Aqueous extracts of V26 stigmas and pollen were treated with 0.025 units of papain for 30 min at 37° C. in a 100 $\mu$l reaction volume. Enzyme activity was verified by treating BSA (0.5 mg/ml) under the same conditions and by examining the digestion products by SDS-polyacrylaminde gel electrophoresis (PAGE). Neither the protease nor a heat treatment (100° C., 5 min) eliminated the ability of the extracts to rescue CMF pollen germination and tube growth.

Collectively, these results indicate that the flavonoids present in wild type pollen play a role in pollen germination and that the wild type stigma contains similar compounds which can compensate for the lack of flavonoids in the CMF pollen.

EXAMPLE 5

Flavonol Rescue of CMF Fertility

Figure 4:
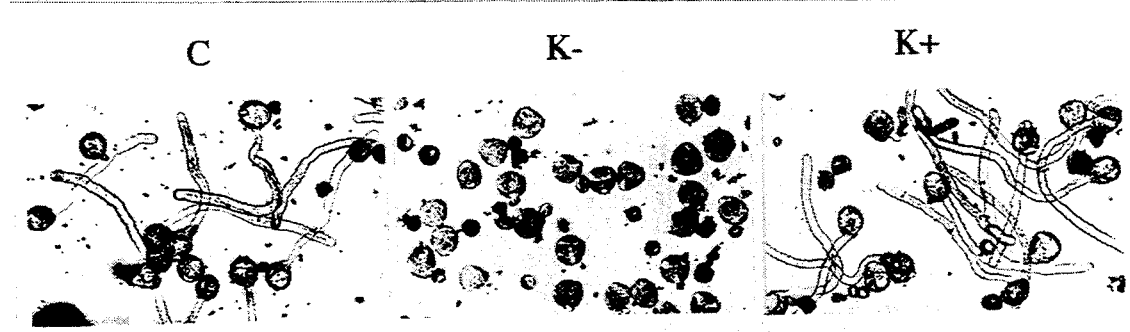
FIG. 4 is a photographic representation of the restoration of pollen germination and tube growth to petunia CHS-deficient pollen by the fertility restoring flavonol, kaempferol. Pollen was collected from conditionally male fertile anthers, suspended in germinating medium, and kaempferol (K+) or DMSO (K−) added to 1 μM final concentration. Representative fields of pollen are pictured after 4 hours of incubation. The germination and tube growth observed in the kaempferol rescued CMF pollen (K+) is indistinguishable from the wild type V26 control (C) which received DMSO only. The nonsupplemented CMF pollen (K−) shows swelling at the germination pore in some grains but no pollen tubes are extruded

Biochemical complementation of the flavonoid-deficient pollen of Example 1 was achieved by adding a low concentration (1 $\mu$M) of kaempferol, a flavonol aglycone, to a suspension of CMF pollen in germination medium (GM). As shown in FIG. 4, side-by-side comparisons made throughout a 12 hour growth period confirmed that germination initiated simultaneously and that tube growth proceeded at the same rate and to the same extent in the rescued CMF pollen (K+) compared to wild type V26 pollen which received no flavonol supplement (C). The rescue was nearly complete; the flavonoid-supplemented pollen showed an 80% germination frequency relative to V26 pollen. CMF pollen to which only the DMSO solvent was added (K−) showed no significant germination (1–2%) and the pollen tubes, if they germinated at all, never progressed more than 2 pollen grain diameters.

Figure 5:
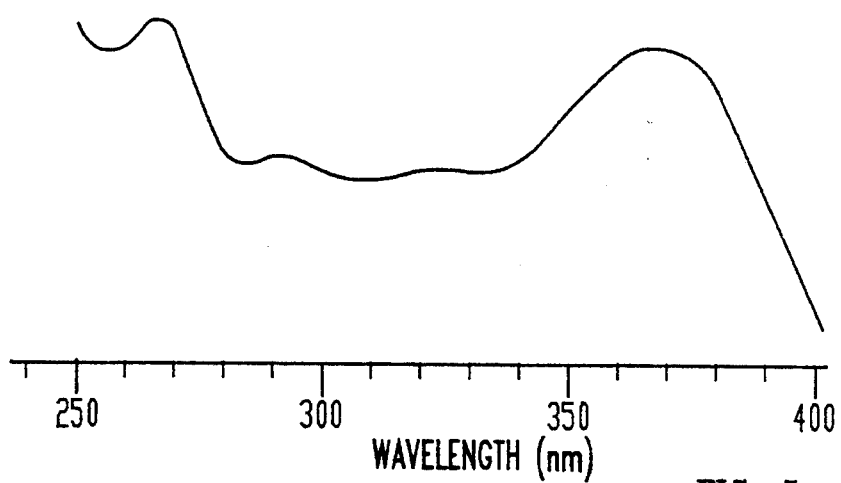
FIGS. 5, 5A and 5B are HPLC profile of methanolic extracts of wild type V26 stigmas (FIG. 5A) and CMF stigmas (FIG. 5B). Absorption at 360 nm of 100 μl aliquots of extracts prepared from 150 stigmas and fractionated in a methanol-water gradient on a reverse-phase $C_{18}$ column. The inset of FIG. 5A is the UV/visible spectrum of the peak at 33.17 min and is identical to that produced by an authentic kaempferol standard. An HPLC profile and UV/visible spectrum of an acid hydrolyzed V26 stigma extract indicates that the major peaks at retention time 7.43, 10.10, 13.46 and 16.65 are glycosides of kaempferol and quercetin.
Figure 5A:
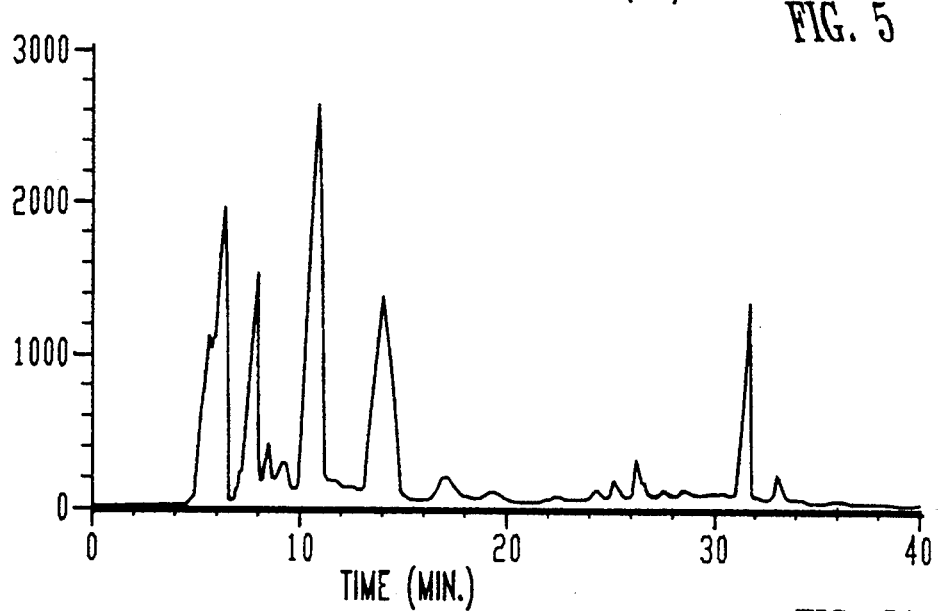
Figure 5B:
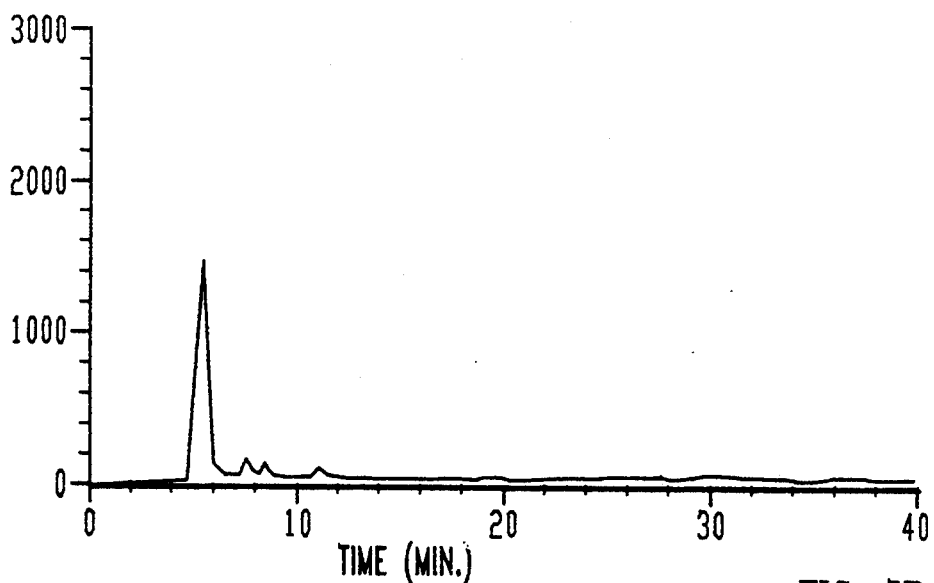

To confirm that wild style stigma extracts which are capable of rescuing pollen germination and tube growth contain kaempferol, unhydrolyzed extract was fractionated by HPLC and analyzed by UV/visible absorption spectroscopy. A peak with a retention time and typical flavonol spectra (absorption maxima around 260 and 360 nm) was detected in the V2 stigma extract (FIG. 5A and inset). This putative kaempferol peak was collected, evaporated to dryness, resuspended in DMSO and added to the in vitro GM media where it elicited a full germination and tube growth response from the CMF pollen. Rechromatography of this active fraction with an authentic kaempferol standard confirmed its purity and identity. From this analysis of 150 stigmas, the amount of kaempferol in a V26 stigma is calculated to be 60 ng/stigma. By assuming a stigma volume of 34 $\mu$l (volume displacement), the flavonol concentration in a V26 stigma is about 6 $\mu$M, a level which is capable of eliciting a strong germination response. An identical analysis on extracts from a pool of 150 CMF stigmas or from 500 CMF anthers yielded no peaks giving a typical flavonoid spectra (see FIG. 5B). Extracts from V26 pollen and anthers produced a chromatogram similar to that shown in FIG. 5 and the eluent peak, with a retention time and UV/visible spectrum indicative of kaempferol, when added to CMF in GM fully stimulated pollen germination. This analysis confirms that kaempferol is present in wild type pollen and anthers.

Structural Features Required For Pollen Rescue Activity

Wild type pollen and stigma extracts from petunia contain other compounds in addition to kaempferol which may also stimulate pollen germination and tube growth (see FIG. 5A). Therefore representative compounds from all the major classes of flavonoids: flavones, flavonones, flavonols, isoflavonoids, chalcones, anthocyanins, and catechins were assayed for pollen rescue activity as follows. Petunia pollen grains were suspended in PEG 4000 germination medium (GM) at a density of $1-2\times10^4$/ml, and 100 µl aliquots of the suspension were placed in wells of a 96 well microtiter plate and were incubated at room temperature with shaking at 150 rpm. Any supplements were added directly to the GM before addition to the pollen. Stock solutions of flavonoids and other chemicals were made directly in dimethylsulfoxide (DMSO) and added to each well to the final concentrations indicated in the following Table 4. The concentration of DMSO was held constant in each essay at 1%. Pollen was scored as germinated when the tube was more than 1 pollen grain diameter long. Practically all grains that germinate go on to produce a tube longer than 5 pollen grain diameters. Petunia V26, as described in Example 1, produces two types of mature pollen; about 25% of the grains are small with no internal features and they never germinate in vitro. Therefore, complete germination in V26 occurs when 75% of the total pollen grains have germinated. The CMF petunia pollen of Example 1 maintains this same ratio. In most rescue experiments the maximum germination frequency was 89% of the viable grains. After 4 hours incubation a minimum of 1000 pollen grains were scored in each assay. The lowest concentration of the tested compounds required to obtain a germination response are set forth in the following Table 3, wherein NR indicates no response. Compounds which cause <20% germination at 100 µM are indicated as >100 µM. In addition to the compounds listed in Table 3, the non-flavonoids p-coumaric acid, salicylic acid, hydroquinone, chlorogenic acid, dihydroascorbic acid, naphthylphthalmic acid (NPA), 1-napthtalencacetic acid (NAA), indol-3-acetic acid (IAA) and gibberellic acid (GA3) were tested and produce no response.

TABLE 3

| COMPOUND | CONCENTRATION FOR RESPONSE (µM) |
|---|---|
| Flavonols | |
| Galangin | 1 |
| Kaempferol | 1 |
| Iso-rhamnetin | 1 |
| Quercetin | 10 |
| Morin | 10 |
| Myricetin | 100 |
| Fisetin | 100 |
| 3-hydroxyflavone | >100 |

TABLE 3-continued

| COMPOUND | CONCENTRATION FOR RESPONSE (µM) |
|---|---|
| Dihydroflavonol | |
| Taxifolin | >100 |
| Flavone | |
| Flavone | NR |
| 7-Hydroxyflavone | NR |
| Apigenin | NR |
| Luteolin | NR |
| Flavonones | |
| Flavonone | NR |
| Naringenin | NR |
| Eriodictyol | NR |

As can be seen from Table 3, the aglycone flavonols successfully restored maximal germination frequency and tube growth capacity to the CMF pollen but among the other classes of flavonoids only the closely related dihydroflavonol, taxifolin, produced a modest (−18%) response at 100 µM (FIG. 4). Additionally, several classes of non-flavonoid compounds were tested including phenolic acids, anti-oxidants, and plant growth regulators but none were able to rescue pollen germination. Hence, the ability to rescue pollen function at physiologically relevant concentrations appears to reside in the flavonols.

From the range of flavonoids tested, five general structural requirements are identified for pollen germination and tube growth. There are absolute requirements for an unsubstituted hydroxyl group at the 3-carbon position and for a keto group at position 4 in the C ring. A maximal response depends on an unsaturated bond between carbons 2 and 3 in the C ring and the degree of hydroxyl group substitutions in the A and B rings. Most interestingly, flavonols glycosylated through the 3 hydroxyl position are inactive although they are by far the most abundant form of flavonols found in plant tissues, including petunia pollen and stigma. No pollen germination was obtained when quercetin-3-0-glucoside and rutin (quercetin-3-0-rhamnoglucoside) were tested at concentrations up to 100 µM. The requirement for a keto group at position 4 in ring C is indicated by the fact that catechin, which has no keto group lacks activity. A comparison of the relative efficiencies of taxifolin (~18% at 100 µM) and quercetin (~50% at 10 µM) shows that a double bond between carbons 2 and 3 in the C ring increases the response by about 30-fold. A comparison of quercetin with Fisetin or with 3-hydroxyflavone, shows that each additional hydroxyl group at either position 5 or 7 on the A ring increases the response approximately 10-fold. This increase may depend largely on the stabilizing effect of a interaction between the 5 hydroxyl group and the adjacent keto group in ring C. Finally, hydroxyl substitutions on the B ring are not necessary for full activity, and in fact increasing the number of groups actually causes a decrease in the activity (compare kaempferol with quercetin and muricetin). This difference could be due to poor uptake or an increase in nonspecific binding caused by the mare polar nature of flavonols with numerous hydroxyl groups.

Some non-active flavonoids have ben reported to antagonize active flavonoid-induction of nodulation genes in the *Rhizobium*-legume system (Djordjevic, M. A., Redmond, J. W., Batley, M. and Rolfe, B. G., 1987, *EMBO* 6:1173-1179; Peters, N. K., and Long, S. K., 1988, *Plant Physiology* 88:396–400). The compounds that were nonactive in rescuing pollen function were tested for their ability to antagonize the action of the flavonol aglycones, as follows. CMF pollen, as described in Example 1, in GM was exposed to inactive compounds at concentrations of 1 and 10 μM for 30 minutes before adding kaempferol to 1 μM. The experiment was also performed by simultaneously adding both the inactive compound and kaempferol at 1:1 or 10:1 ratios, to the pollen suspension. The pollen germination frequency was scored after 4 hours incubation and no antagonizing action was detected in any of the combinations tested. The following inactive compounds were analyzed: apigenin, chalcone, eriodictyol, flavone, flavanone, luteolin, naringenin, catechin, chlorogenic acid, p-coumaric acid, hydroquinone, and salicylic acid.

EXAMPLE 6

UV Effects

In part because of their UV light absorbing capabilities, flavonoids are postulated to function as UV protectants in plants (W. Jahnen and K. Hahlbroch, 1988, *Planta* 173:453 and references therein). To determine if the lack of germination in the flavonoid-deficient pollent was due to UV effects, dark germination experiments were performed with three variations. Pollen was harvested either from (1) flowers that were collected and stored (in water) in complete darkness for 24 hours or (2) freshly picked flowers. From these two sources pollen suspensions in GM with or without flavonols were prepared in a darkroom using a red safe light. The third variation involved preparing the pollen suspension from the freshly harvested flowers in the light but adding the flavonols solution in the dark. All specimens were wrapped in foil and incubated as described in Example 5. There was no detectable effect of light on germination frequency for either the V26 control or the flavonoid deficient pollen, with or without added flavonols.

To determine if UV light affected self fertilizations, mature plants were grown for several weeks under a 610 nm filter petunia plants as described in L. P. Taylor and W. R. Briggs, 1990, *Plant Cell* 2:115. Petunia buds take about 2 weeks to form and mature, therefore only those buds that formed after the plants were placed under the filter were tested and thus were exposed to no light below 610 nm were self fertilized. No seed set occurred in any of the crosses 910 trials) but all V26 control self crosses performed under the same conditions set full seed pods.

EXAMPLE 7

Effect of Flavonol Exposure Time

The amount of flavonoid exposure required for complete germination and maximal tube growth was determined by varying the time the germination pollen was in the presence of flavonol. A concentration of kaempferol calculated to give near maximal rescue, yet easily removed by washing (0.5 μM final), was added to a 60×15 mm petri dish containing a suspension of flavonoid-deficient pollen in GM and the resulting suspension was continuously rotated at 150 rpm. At the times indicated in Table 4, 400 μl aliquots were taken, centrifuged, washed in 1 ml GM to remove the kaempferol, recentrifuged, resuspended in 400 μl GM, and split into two portions. One 100 μl aliquot was again supplemented to 0.5 μM kaempferol (control) but the other portion was allowed to continue growth without additional flavonol exposure (treated). Growth was allowed to proceed for a total elapsed time of 4 hours from the formulation of the original suspension, then germination frequency and tube length were scored in both treated and control germinations. The results are shown in the following Table 4:

TABLE 4

| Exposure time (min) | Treated Pollen Germination (%)* | Tube Length** | Control Germination (%)* |
|---|---|---|---|
| 0 | 3.7 + 1.5 | 2× | 48.3 +/− 2.5 |
| 10 | 6.6 +/− 2.7 | 2× | 55.5 +/− 8.6 |
| 20 | 15.7 +/− 9.2 | 2–3× | 47.9 +/− 7.0 |
| 30 | 13.8 +/− 1.7 | 2–3× | 44.4 +/− 3.7 |
| 60 | 38.9 +/− 2.9 | 3× | 48.4 +/− 1.3 |
| 120 | 47.3 +/− 3.6 | >5× | 47.7 +/− 2.2 |

*mean +/− SEM, n = 3
**relative to pollen grain diameter

As seen in Table 4, a measurable increase in germination was detected with an exposure time as short as 10 minutes (Table 1). An exposure time between 1 to 2 hours was required for maximal germination frequency and tube length.

EXAMPLE 8

In vivo Fertility Rescue

The ability to restore self fertility to the CMF petunia by supplying the flavonol aglycone to the pollen at the time of pollination was tested by scoring for successful fertilizations resulting from self crosses of the CMF petunia done in the presence of added flavonols. Prior to self pollinating, flavonol aglycones were applied either (i) directly to the stigma or (ii) mixed with the freshly collected pollen. The most successful technique, measured by the quantity of seed set, required application of the flavonol to the stigma 12–16 hours prior to self pollination. 47 self crosses were performed with added kaempferol or quercetin, and nearly 60% (27 out of 47) produced seed pods. The number of seeds per pod varied from 31 to 287, and in germination tests >90% of the seeds in any single pod were viable. All self crosses done without added flavonols (>30 trials) yielded no seed set.

The dominant CMF trait exhibited by the flavonoid-deficient petunia is tightly linked to a second dominant gene conferring kanamycin resistance (KAN) (Napoli, C., Lemieux, C. and Jorgensen, R., 1990, "Introduction to a Chimeric Chalcone Synthase Gene Into Petunia Results in Reversible Co-repression of Homologous Genes in Trans," *Plant Cell* 2:279–289). The KAN marker was used to test for segregation of the CMF character in the seeds produced by self crossing the flavonoid-deficient plants in the presence of added flavonol. Freshly harvested seeds were surface sterilized in 20% bleach, washed with sterile water and soaked for 30 min in 100 ppm GA3 solution before plating on germination plates (1×MS, 3 mM MES [pH 5.6], 1×B5 vitamin mix, 3% sucrose and 0.2% solidifying agent) containing 100 μg/ml kanamycin. After growth at 23° C. supplemented with a 16/8 hour photoperiod, resistance to kanamycin was scored by screening by seedlings sensitive to kanamycin. In the following Table 5, P-value represents the observed level of significance for a one degree of freedom chisquare goodness-of-fit test.

TABLE 5

| Pod | Seedlings Total | KAN | KAN | P(3:1) |
|---|---|---|---|---|
| 1 | 75 | 58 | 17 | 0.74 |
| 2 | 65 | 50 | 15 | 0.83 |
| 3 | 81 | 59 | 22 | 0.75 |

Seeds germinated in the presence of 100 μg/ml kanamycin segregated in a 3:1 ratio of KAN resistance: sensitive as expected for a heterozygous dominant trait, as shown in Table 5.

EXAMPLE 9

Field Trial

A field trial was performed using a naturally occurring flavonoid-deficient maize mutant, white pollen, defective in flavonoid activity, which produces white, non-functional pollen, and is self sterile (E. H. Coe, S. M. McCormick, S. A. Modena, 1981, *J. Hered.* 72:318). A total of 45 self crosses were performed in the presence of added flavonoids and all of them (100%) produced fully filled ears while self crosses (45 trials) done without added flavonoids showed seed set less than 1% of normal. The maize white pollen plants used had stable recessive mutations at C2 and Whp introgressed into a W23 inbred background. The white pollen plants (c2/c2 whp/whp) were maintained by crossing with pollen from isogenic plants carrying a single functional copy of CHS (C2/c2 whp/whp). The plants were male sterile in self and sibling crosses and produced no visible flavonoid pigments in any tissues, including pollen and seeds. Standard genetic field practices were employed to insure that no contaminating pollen reached the silks of the white pollen plants. In addition, the white pollen block was surrounded with a pigmented kernel variety so that any contaminating kernels would immediately be recognized. Mutant white pollen from 50-100 plants was collected from the tassel bags, pooled, and divided into 2 portions. One portion was used "as is" for crosses and the other was mixed in an approximate 20:1 ratio with dry flavonoids (either quercetin, kaempferol, or a 50:50 mixture of the two). Prepared white pollen silks were pollinated with either the untreated or the flavonoid-supplemented white pollen and bagged immediately. The mature ears were harvested 45 days after pollination. White pollen crosses usually set ~200 kernels per ear and this number was routinely obtained in the biochemically complemented self-crosses. A total of 45 self crosses were performed in the presence of added flavonols and all of them (100%) produced fully filled ears while self crosses (45 trials) done without added flavonols showed seed set less than 1% of normal.

The foregoing experiments confirm that flavonoids are required for pollen function as follows: (i) methanol and aqueous extracts of wild type stigmas and pollen can fully restore germination and tube growth to flavonoid-deficient pollen; (ii) these extracts contain the same flavonols that show activity in the in vitro fertility rescue assay described herein; (iii) the ability to rescue pollen germination and restore full tube growth in vitro and full seed in vivo is restricted to a specific class of flavonoid, the flavonol aglycones; (iv) the effective concentration of flavonol varies with structural features, but several compounds show a pronounced effect at levels less than 10 μM, well within physiological concentrations of these compounds.

Flavonoids are produced by virtually all classes of plants from liverworts, mosses, and ferns to gymnosperms and angiosperms. Past flavonoid surveys often used dried leaf or root tissue from herbarium specimens; consequently, we do not have a good indication of how widespread is the occurrence of pollen flavonoids. Their ubiquitous presence in plant tissues and the fact that flavonoids have been identified in pollen extracts from several widely divergent species, would argue that flavonoids are a universal constituent of pollen. Most plant flavonols occur at the 3-0-glycosylated species (J. B. Harbome and C. A. Williams, 1988, in *The Flavonoids, Advances in Research Since 1980* J. B. Harbome, Eds. (Chapman and Hail, London) chaps. 7, 8), and this is the predominant form in petunia pollen (O. Ceska and E. D. Styles, 1984, *Phytochemistry* 23:1822). Only the aglycone form can rescue pollen function which suggests that either low non-detected levels of the aglycone are normally present, or glycosidase activity is required to produce the aglycones that are necessary for fertilization.

Pollen provides the natural access point to manipulate the fertilization process. The loss of flavonoid expression resulting in CMF plants acts as a natural gametostat and not a gametocide. Full male function can be restored by external application of flavonols to the flavonoid-deficient pollen. In addition to the identification of a factor involved in higher plant fertilization, a significant benefit is in the development of a reversible male sterile system for the production of hybrid seed.

By connecting a gene affecting flavonol production to an inducible promoter, in accordance with the invention described herein, sterility may be controlled. One such gene already known involves the CHS genus, c2 and Whp described by Coe, et al., Supra incorporated herein by reference. Alternatively, the F3H gene may be isolated by generating a hybridization probe using PCR oligonucleotide primers (see Saiki, R. K., 1990, supra) based on the published Antirrhinum F3H sequence.

Thus, by using a gene which controls production of flavonols as herein described, one can control sterility.

In general, in accordance with the invention described herein, a gene regulating flavonol production can be incorporated into the plant along with a necessary promoter which is inducible. The plant will be sterile since the critical flavonol is not produced, and when the promoter is induced, the plant will be fertile. The native gene producing flavonol i s a normally fertile plant which may be inactivated by any of a variety of methods described below, such as backcrossing or homologous recombination.

Inducible Promoters

In the practice of this invention the promoter region is removed from a cloned gene responsible for male fertility and is replaced with a promoter that only responds to a specific external stimulus. Thus, the gene will not be transcribed except in response to the external stimulus. As long as the gene is not being transcribed, its gene product—which is necessary for completion of pollen development—is not produced. This causes a breakdown in one or more of the biochemical/physiologic pathways of pollen development, which results in male sterility. The plant can only become fertile under the specific stimulus that activates the selected promoter.

An example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Wiegand, et al., "Messenger RNA Encoding a Glutathione-S-Transferase Responsible for Herbicide Tolerance in Maize is Induced in Response to Safener Treatment". Plant Molecular Biology 7: 23514 243, 1986). It has been discovered that treating maize seed with GSTs increases the tolerance of the maize to the herbicides. Studies have shown that the GSTs are directly involved in causing this enhanced tolerance. This action is primarily mediated through a specific 1.1 kb mRNA transcription product. In short, maize has a naturally occurring quiescent gene already present that can respond to GSTs and that can be induced to produce a gene product. This gene has already been identified and cloned. Thus, in one embodiment of this invention, the promoter is removed from the GST responsive gene and attached to the male fertility gene that previously has had its native promoter removed. This engineered gene is the combination of a promoter that responds to an external chemical stimulus and a gene responsible for successful development of fertile pollen.

Gene Introduction

Several methods are known in the art for transferring cloned DNA into maize. These include electroporation-facilitated DNA uptake by Maize protoplasts (Rhodes et al., "Genetically Transformed Maize Plants from Protoplasts", *Science*, Vol. 240 (8 Apr. 1988); treatment of maize protoplasts with polyethylene glycol (Lyznik et al., "Stable Co-Transformation of Maize Protoplasts with Gus A and Neo Genes", *Plant Molecular Biology* 13: 151–161, 1989); and bombardment of maize cells with DNA laden microprojectiles (Klein, et al., "Genetic Transformation of Maize Cel is by Particle Bombardment", *Plant Physiol.* (1989) 91,440–444) and Klein, et al., "Factors Influencing Gene Delivery into Zea Mays Cells by High-Velocity Microprojectiles", *Bio/Technology* Vol. 6 May 1988), all incorporated by reference.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in the the publication of Bowen, et al., "R genes as visual markers for corn transformation," Abstract, edit. Gallagher, Academic Press (Oct. 1989) and Ludwig, et al., "A regulatory gene as a novel visible marker for maize transformation," *Science,* 247:449–450 (Jan. 26, 1990). This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either maize protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

It will be readily accepted by those skilled in he art that the native fertility gene will be enabled by the process described. Homologous recombination will replace the native gene. Another method of inactivating the native gene is through well known backcrossing techniques, one example of which is described in Example 9.

As a specific alternative, the gene encoding F3II, CHI or CHS in a plant may be removed, blocked or otherwise impaired to prevent expression of the F3H enzyme in the plant. In addition to blocking the synthesis of F3II in vivo, it will also be apparent that F3H activity may be blocked with moleties that interact directly with F3H to inactivate or impair its hydroxylase activity. In addition, the production of flavonols may be impaired by blocking CHI activity; however this alternative is less preferred since the conversion of chalcononaringenin to naringenin proceeds spontaneously at a low rate in the absence of CHI. This is but one of a variety of embodiments falling within the scope of the invention described.

Sterility Selection And Fertility Restoration

After the gene is introduced into a plant, the appropriate plant types are selected, that is plants that are male sterile. These plants are male sterile because the isolated and cloned male fertility gene does not have its native promoter and, therefore, is not producing its gene product that is crucial to successful pollen development. Therefore, the engineered gene acts as a recessive mutant allele of that gene. In normal plant biotechnology, once the desired genotype is identified following transformation and regeneration, the plants are selfed to recover that genotype. However, in the practice of this invention, the desired genotype cannot be selfed at the first generation because it is male sterile. To obtain progeny, fertility must be induced by spraying the plants with a compound which induces transcription of the gene by activating the altered promoter. In the case of the GST promoters, the compound is preferably a GST-inducing compound such as N,N-diallyl-2-2-dichloroacetanide. The promoter attached to the male fertility gene responds to this chemical and causes the transcription of the gene to begin. Once this occurs, the normal gene product is produced from the gene and some level of male fertility is induced. Pollen from this plant is then used to effect pollination of the original selected genotype.

Once the initial isolation and propagation of the desired genotype is completed, the procedure is more straightforward. Only inbreds that are used as female parents in hybrid crosses are transformed into male sterile variants. Once they are transformed, the amount of male sterile/female fertile seed must be increased. This is accomplished by planting in an isolated area (away from other maize pollen) and spraying with a chemical to which the promoter responds. Spraying induces the promoter to start transcription of the gene attached to it. This will produce some degree of fertility. A particular advantage of this system in comparison to systems such as that disclosed in PCT publication WO89/10396 of Mariani et al (based on Intl. Appl. No. PCT/EP89/00495), in which sterility is induced, is that the treatment does not have to be 100% effective, because normally much more pollen is produced by a maize plant than is actually needed for fertilization of all available silks. Therefore, even low fertility restoration will be effective in obtaining acceptable levels of seed increase. At the same time, self-pollination does not occur in hybrid seed production because the plants of this invention are normally male sterile and must be treated to become fertile. In systems in which sterility is induced, induction of sterility must be 100% effective to avoid self-pollination when hybrid seed is produced.

All the seed harvested continues to be homozygous and sterile since the fertility is only restored in a single parent generation by treatment with the fertility inducing chemical. This seed is then used in a hybrid production field where it is used as a female parent. Because the plants are male sterile, they do not have to be detasseled. All of the hybrid plants produced from such seed are male fertile because the resulting progeny inherit one modified gene from the female parent and one normal gene from the male parent. Normal pollen production occurs.

While the foregoing illustrates the preferred embodiment of the invention, it will be appreciated that various changes can be made without departing from the spirit and scope of the invention.

What is claimed is:

1. A method for providing heritable, externally controllable male sterility in a plant, comprising the steps of:
   a) selecting a gene which affects flavonol production in a plant;
   b) cloning the selected gene;
   c) linking the cloned gene in an expression sequence with an inducible promoter responsive to external control;
   d) inserting the expression sequence into the nuclear genome of the plant; and
   e) inactivating the gene which codes for the gene product of the cloned gene from the native nuclear genome of the plant.

2. The method of claim 1 wherein the flavonol biosynthetic pathway gene is involved in the expression of a compound of the formula:

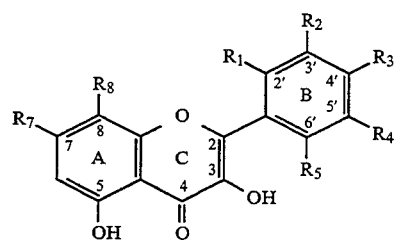

wherein $R_1$, $R_2$, $R_3$, $R_4$, $R_5$, $R_7$, and $R_8$ are hydrogen, hydroxyl or alkoxy having from one to three carbon atoms.

3. The method of Claim 2 wherein not more than two of $R_1$–$R_5$ are hydroxyl or methoxy and the remaining $R_1$–$R_5$ are hydrogen, and $R_7$ and $R_8$ are hydrogen, hydroxyl or methoxy.

4. The method of claim 2 wherein the fertility restoring flavonol is selected from the group galangin, kaempferol, iso-rhamnetin, quercetin and morin.

5. The method of claim 1 wherein the fertility affecting flavonone is a flavonone-3-hydroxylase.

6. A method of reproducing a plant having heritable, externally controllable male sterility resulting from replacement of a gene which affects flavonol production in the plant with a gene which coats for the same gene product, but which is linked in an expression sequence with an inducible promoter responsive to external control, comprising the steps of:
   a) planting seed of the plant to provide growing, male sterile plants;
   b) inducing conversion of the growing plants to male fertile form by growing the plants under conditions which induce the promoter to express the gene coding for the same flavonol gene product;
   c) open-pollinating the growing plants in isolation to produce seed; and
   d) harvesting the seed.

7. The method of Claim 6 wherein the flavonol is a compound of the formula:

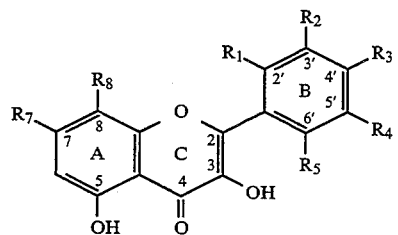

wherein $R_1$, $R_2$, $R_3$, $R_4$, $R_5$, $R_7$, and $R_8$ are hydrogen, hydroxyl or alkoxy having from 1 to 3 carbon atoms.

8. The method of Claim 7 wherein not more than two of $R_1$–$R_5$ are hydroxyl or methoxy and the remaining $R_1$–$R_5$ are hydrogen, and $R_7$ and $R_8$ are hydrogen, hydroxyl or methoxy.

9. The method of claim 7 wherein the fertility restoring flavonol is selected from the group galangin, kaempferol, iso-rhamnetin, quercetin and morin.

10. The method of claim 6 wherein the fertility affecting flavonone is a flavonone-3-hydroxylase.

11. A method of producing hybrid seed, comprising the steps of
   a) planting, in cross pollinating juxtaposition, a first seed from a selected male fertile male parent line and a second seed from a selected female parent line having male sterility resulting from replacement of a gene which affects flavonol production with a gene which affects flavonol production linked in an expression sequence with an inducible promoter responsive to external control, b) growing the seed to mature plants under conditions which do not induce expression of the gene;

c) cross pollinating the male sterile female plant with pollen from the male-fertile male plant; and c) harvesting hybrid seed from the male-sterile female plant.

12. The method of Claim 11 wherein the flavonol is a compound of the formula:

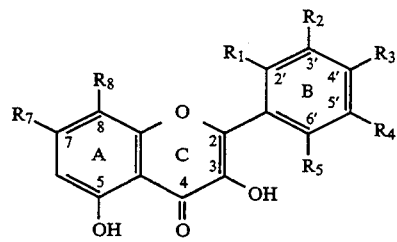

wherein $R_1$, $R_2$, $R_3$, $R_4$, $R_5$, $R_7$, and $R_8$, are hydrogen, hydroxyl or alkoxy having from 1 to 4 carbon atoms.

13. The method of Claim 12 wherein not more than two of $R_1$–$R_5$ are hydroxyl or methoxy and the remaining $R_1$–$R_5$ are hydrogen, and $R_6$ and $R_7$ are hydrogen, hydroxyl or methoxy.

14. The method of claim 12 wherein the flavonol is selected from the group galangin, kaempferol, isorhamnetin, quercetin and morin.

15. The method of claim 11 wherein the flavonone is a flavonone-3-hydroxylase.

* * * * *

UNITED STATES PATENT AND TRADEMARK OFFICE
CERTIFICATE OF CORRECTION

PATENT NO. : 5,432,068

DATED : July 11, 1995

INVENTOR(S) : Marc C. Albertsen, Larry R. Beach, John Howard, Gary A. Huffman and Loverine Taylor It is certified that error appears in the above-identified patent and that said Letters Patent is hereby corrected as shown below:

Title page, item [73], should read--
  Assignee: Pioneer Hi-Bred International, Inc.
        Des Moines, Iowa and Washington State University Research
         Foundation, Inc.
        Pullman, Washington --

Signed and Sealed this

Twenty-fourth Day of September, 1996

Attest:

BRUCE LEHMAN

*Attesting Officer*     *Commissioner of Patents and Trademarks*